United States Patent [19]

Boisvenue et al.

[11] Patent Number: 5,618,547

[45] Date of Patent: Apr. 8, 1997

[54] CONTROL OF ECTOPARASITES

[75] Inventors: Rudolph J. Boisvenue, Greenfield; Gary D. Crouse, Indianapolis, both of Ind.

[73] Assignee: British Technology Group Limited, London, England

[21] Appl. No.: 208,199

[22] Filed: Mar. 10, 1994

Related U.S. Application Data

[60] Continuation of Ser. No. 373,121, Jun. 28, 1989, abandoned, which is a division of Ser. No. 123,453, Nov. 20, 1987, Pat. No. 4,870,109, which is a continuation-in-part of Ser. No. 916,977, Oct. 9, 1985, abandoned, which is a continuation of Ser. No. 736,177, May 20, 1985, abandoned.

[51] Int. Cl.$^6$ ..................................................... A01N 25/00
[52] U.S. Cl. ..................... 424/405; 424/408; 424/409; 424/410; 424/422; 424/442; 424/464; 424/451; 424/438; 424/486; 514/683; 514/684; 514/688
[58] Field of Search ..................... 514/444, 448, 514/685, 688, 683, 684; 424/405, 485, 488, 408, 409, 410, 486

[56] References Cited

U.S. PATENT DOCUMENTS

| | | | |
|---|---|---|---|
| 2,107,298 | 2/1938 | Kilgore | 514/685 |
| 3,362,935 | 1/1968 | Norton | 260/63 |
| 3,636,214 | 1/1972 | Clark | 424/245 |
| 3,647,712 | 12/1972 | Lucid . | |
| 3,700,416 | 3/1972 | Lucid . | |
| 3,742,062 | 6/1973 | Chapellow, Jr. | 75/117 |
| 3,764,274 | 10/1973 | Lucid | 75/101 BE |
| 4,268,497 | 5/1981 | Griffin et al. | 424/438 |
| 4,273,920 | 6/1981 | Nevin | 528/361 |
| 4,544,547 | 10/1985 | Von Bittera et al. | 424/78 |
| 4,665,100 | 5/1987 | Ludwig | 514/778 |

FOREIGN PATENT DOCUMENTS

| | | | |
|---|---|---|---|
| 862068 | 1/1971 | Canada . | |
| 4414 | 6/1986 | Dominican Rep. . | |
| 202903 | 11/1986 | European Pat. Off. . | |
| 714221 | 6/1971 | South Africa | 424/245 |
| 2122493 | 1/1984 | United Kingdom | 424/43 |

OTHER PUBLICATIONS

Jones, *Veterinary Pharmacology and Therapeutics*, Iowa State University Press, pp. 14–16 (1965).
*Remington's Pharmaceutical Sciences*, 16th ed., Mack Publishing Company, p. 1252 (1980).
*Chemical Abstracts*, 95 203495z (1981).
*Chemical Abstracts*, 93, 71207d (1980).
Reid & Calvin, "Some New β–Diketones Containing the Trifluoromethyl Group", *J.A.C.S.* 72, 2948 (1950).
Massyn et al., "Localisation de l'hydroxyle enolique dans les β–dicetones perfluoroalkylees", *Bulletin De La Societe Chimique De France*, 5–6, 190, 975 (1974).
*Chemical Abstracts*, 97, 91361k (1982).

*Primary Examiner*—Neil S. Levy
*Attorney, Agent, or Firm*—Nixon & Vanderhye

[57] ABSTRACT

A series of 1,3-propanediones having a perfluoroalkyl group or a perfluorocycloalkyl group on one carbonyl, and a 3,5-disubstituted phenyl group on the other, are useful when administered to animals for the control of ectoparasites.

31 Claims, No Drawings

CONTROL OF ECTOPARASITES

This is a continuation of application Ser. No. 07/373,121, filed Jun. 28, 1989, now abandoned, which is a division of application Ser. No. 07/123,453, filed Nov. 20, 1987, now U.S. Pat. No. 4,870,109, which is a CIP of application Ser. No. 06/916,977, filed Oct. 9, 1985, now abandoned, which is a continuation of application Ser. No. 06/736,177, filed May 20, 1985, now abandoned.

BACKGROUND OF THE INVENTION

1. Field of the Invention

The present invention belongs to the fields of agricultural chemistry and animal husbandry, and provides new 1,3-propanediones which have a 3,5-disubstituted phenyl group, and a $C_2$–$C_4$ perfluoroalkyl or $C_3$–$C_6$ perfluorocycloalkyl group, on the carbonyls. The novel compounds are useful in controlling ectoparasites of economic and companion animals.

2. State of the Art

The control of ectoparasites, such as fleas, ticks, biting flies and the like, has long been recognized as an important problem in animal husbandry. The traditional treatments for domestic animals were topically applied insecticides, such as the famous dips for sheep. Indeed, such treatments are still in wide use. However, the more modern thrust of research has been towards compounds which can be administered to the animals, especially orally, and which will control ectoparasite populations by poisoning individual parasites when they ingest the blood of the treated animal.

In the art, Lindberg et al., South African Patent 71/4221, disclose insecticidal activity of 1,3-propanediones having a trifluoromethyl group on one carbonyl, and a substituted phenyl group on the other carbonyl. Ectoparasiticidal use of some of their compounds is disclosed.

Cahoy, Canadian Patent 862,068, shows a group of 1,3-propanediones, having a phenyl or napthyl group on one carbonyl and a perhalomethyl or perhaloethyl group on the other carbonyl. Cahoy shows his compounds to be insecticides but does not refer to treatment of animals.

Clark, U.S. Patent 3,636,214, shows some 1,3-propanediones having an aryl group on one carbonyl, and a trifluoromethyl or other haloalkyl group on the other carbonyl. Clark, however, prefers use of his compounds in the form of copper chelates, and only for the purpose of controlling fungi, especially in the soil.

SUMMARY OF THE INVENTION

The present invention provides compounds of the formula

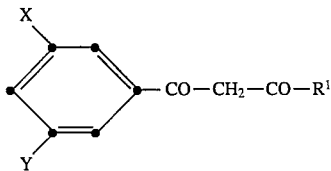

wherein $R^1$ is a $C_2$–$C_4$ perfluoroalkyl or a $C_3$–$C_6$ perfluorocycloalkyl;

X and Y are each independently chloro, bromo, fluoro, or trifluoromethyl; with the proviso that if $R^1$ is $C_2F_5$, X and Y cannot both be chloro; and the sodium, potassium or lithium salts thereof.

The present invention also provides a method of controlling a population of insect or acarina ectoparasites which consume blood of a host animal which comprises administering to the host animal an effective amount of a compound of the formula

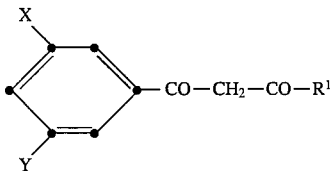

wherein $R^1$ is a $C_2$–$C_4$ perfluoroalkyl or a $C_3$–$C_6$ perfluorocycloalkyl;

X and Y are each independently chloro, bromo, fluoro, or trifluoromethyl; or a sodium, potassium or lithium salt thereof.

DESCRIPTION OF THE PREFERRED EMBODIMENTS

Throughout the present document, all temperatures are expressed in degrees Celsius. All expressions of percentage, concentration and the like are in weight units unless otherwise described.

The terms "perfluoroalkyl" and "perfluoro-cycloalkyl" refer to alkyl or cycloalkyl groups in which all, or all but one, of the hydrogen atoms have been replaced by fluorine atoms. Thus, the $R^1$ groups of the compounds of the present invention include perfluoroalkyl and perfluorocycloalkyl groups such as —$CF_2CF_3$, —$CF_2CF_2H$, —$CFHCF_3$, —$CF_2CF_2CF_3$, —$CF_2CF_2CF_2H$, —$CF_2CFHCF_3$, —$CF_2 CF_2 CF_2 CF_3$, —$CF_2 CF (CF_3)_2$, —$CF_2 CF_2 CF_2 CF_2 H$, —$CF_2 CF (CF_2 H) CF_3$, —$CF_2 CF_2 CFHCF_3$, —$CF_2 CH (CF_3)_2$, 1,2,2,3,3-pentafluorocyclopropyl, 1,2,2,3-tetrafluorocyclopropyl, 2,2,3,3-tetrafluorocyclopropyl, 1,2,2,3,3,4,4-heptafluorocyclobutyl, 1,2,2,3,4,4-hexafluorocyclobutyl, 1,2,2,3,3,4-hexafluorocyclobutyl, 1,2,2,3,3,4,4,5,5-nonafluorocyclopentyl, 1,2,2,3,3,4,5,5-octafluorocyclopentyl, 2,2,3,3,4,4,5,5-octafluorocyclopentyl, 1,2,2,3,3,4,4,5,5,6,6-undecafluorocyclohexyl, 1,2,2,3,3,4,4,5,5,6-decafluorocyclohexyl, 1,2,2,3,3,4,5,5,6,6-decafluorocyclohexyl, and the like.

While all of the compounds described above are potent ectoparasiticides, certain compounds are preferred. Preferred compounds of the present invention are those wherein $R^1$ is $C_2$–$C_4$ perfluoroalkyl. Especially preferred compounds of the present invention are those wherein $R^1$ is $C_2$–$C_3$ perfluoroalkyl. Even more preferred compounds are those wherein $R^1$ is $C_2$–$C_3$ perfluoroalkyl and X and Y are chosen from the group consisting of:

a.) X is chloro and Y is chloro;

b.) X is bromo and Y is bromo;

c.) X is fluoro and Y is fluoro; and d.) sodium, potassium or lithium salts of the above compounds.

The most preferred compounds of the present invention are those compounds wherein $R^1$ is $C_2$–$C_3$ perfluoroalkyl; X and Y are both chloro; and the sodium, potassium, or lithium salts thereof. Particularly preferred compounds, among these most preferred compounds, are 1-(3,5-dichlorophenyl)-3-(1,1,2,2,3,3,3-heptafluoropropyl)-1,3-propanedione and 1-(3,5-dichlorophenyl)-3-(1,1,2,2-tetrafluoroethyl)-1,3- propanedione, and the sodium, potassium or lithium salts thereof.

Preferred compounds for use in the method for controlling ectoparasites of this invention are those wherein $R^1$ is $C_2$–$C_4$ perfluoroalkyl. Especially preferred compounds for use in the method of the present invention are those wherein $R^1$ is $C_2$–$C_3$ perfluoroalkyl. Even more preferred compounds for use in the presently claimed method are those wherein $R^1$ is $C_2$–$C_3$ perfluoroalkyl and X and Y are chosen from the group consisting of:

a.) X is chloro and Y is chloro;
b.) X is bromo and Y is bromo;
c.) X is fluoro and Y is fluoro; and
d.) sodium, potassium or lithium salts of the above compounds.

The most preferred compounds for use in the method for controlling ectoparasites of this invention are those wherein $R^1$ is $C_2$–$C_3$ perfluoroalkyl; X and Y are both chloro; and the sodium, potassium or lithium salts thereof. Particularly preferred compounds, among these most preferred compounds, in the method of the present invention are 1-(3,5-dichlorophenyl)-3-(1,1,2,2,3,3,3-heptafluoropropyl)-1,3-propanedione, 1-(3,5-dichlorophenyl)-3-(1,1,2,2,2-pentafluoroethyl)-1,3-propanedione, and 1-(3,5-dichlorophenyl)-3-(1,1,2,2-tetrafluoroethyl)-1,3-propanedione, and the sodium, potassium or lithium salts thereof.

Use of any of the above compounds, especially the most preferred compounds enumerated above, in the form of their salts, especially the sodium salt, is particularly preferred in the method for controlling ectoparasites of this invention.

While the compounds of the present invention are consistently named as 1,3-propanediones in the present document, it will be understood that it is quite possible if not probable that one of the carbonyl groups will actually be in the enol form. That is to say, the compound will exist in a form described as follows.

R—CO—CH═C(OH)—R¹

Indeed, it is most probable that the compounds exist in an equilibrium form containing some of the diketone and some of the enol at all times. A careful study of the equilibrium has not been carried out, and so the compounds will be described here as diketones in all cases. It will be understood by the skilled reader that the principles and function of the present invention remain the same, whether carried out with the diketone, with pure enol, or with an equilibrium mixture of the diketone and the corresponding enol.

It is believed that the nature of the compounds used in the present invention has been made entirely clear. However, to assure that the reader fully comprehends the invention, a group of exemplary compounds will be mentioned here.

1-(3,5-dichlorophenyl)-3-(1,1,2,2,2-pentafluoroethyl)-1,3-propanedione
1-(3,5-dichlorophenyl)-3-(1,1,2,2-tetrafluoroethyl)-1,3-propanedione
1-(3,5-dichlorophenyl)-3-(1,1,2,2,3,3,3-heptafluoropropyl)-1,3-propanedione
1-(3,5-dichlorophenyl)-3-(1,1,2,3,3,3-hexafluoropropyl)-1,3-propanedione
1-(3,5-dichlorophenyl)-3-(1,1,2,2,3,3,4,4,4-nonafluorobutyl)-1,3-propanedione
1-(3,5-dichlorophenyl)-3-(1,1,2,2,3,4,4,4-octafluorobutyl)-1,3-propanedione
1-(3,5-dichlorophenyl)-3-(2-trifluoromethyl-1,1,3,3,3-pentafluoropropyl)-1,3-propanedione
1-(3,5-dichlorophenyl)-3-(1,2,2,3,3-pentafluorocyclopropyl)-1,3-propanedione
1-(3,5-dichlorophenyl)-3-(1,2,2,3,3,4,4-hexafluorocyclobutyl)-1,3-propanedione
1-(3,5-difluorophenyl)-3-(1,1,2,2,2-pentafluoroethyl)-1,3-propanedione
1-(3,5-difluorophenyl)-3-(1,1,2,2-tetrafluoroethyl)-1,3-propanedione
1-(3,5-difluorophenyl)-3-(1,2,2,2-tetrafluoroethyl)-1,3-propanedione
1-(3,5-difluorophenyl)-3-(1,1,2,2,3,3,3-heptafluoropropyl)-1,3-propanedione
1-(3,5-difluorophenyl)-3-(1,1,2,2,3,3-hexafluoropropyl)-1,3-propanedione
1-(3,5-difluorophenyl)-3-(1,1,2,2,3,3,4,4,4-nonafluorobutyl)-1,3-propanedione
1-(3,5-difluorophenyl)-3-(2-trifluoromethyl-1,1,2,3,3,3-hexafluoropropyl)-1,3-propanedione
1-(3,5-difluorophenyl)-3-(1,1,2,2,3,3,4,4-octafluorobutyl)-1,3-propanedione
1-(3,5-difluorophenyl)-3-(2-trifluoromethyl-1,1,2,3,3-pentafluoropropyl)-1,3-propanedione
1-(3,5-difluorophenyl)-3-(1,2,2,3-tetrafluorocyclopropyl)-1,3-propanedione
1-(3,5-difluorophenyl)-3-(2,2,3,3,4,4-hexafluorocyclobutyl)-1,3-propanedione
1-(3,5-dibromophenyl)-3-(1,1,2,2,2-pentafluoroethyl)-1,3-propanedione
1-(3,5-dibromophenyl)-3-(1,1,2,2-tetrafluoroethyl)-1,3-propanedione
1-(3,5-dibromophenyl)-3-(1,1,2,2,3,3,3-heptafluoropropyl)-1,3-propanedione
1-(3,5-dibromophenyl)-3-(1,1,2,2,3,3,4,4,4-nonafluorobutyl)-1,3-propanedione
1-(3,5-dibromophenyl)-3-(2-trifluoromethyl1,1,2,3,3,3-hexafluoropropyl)-1,3-propanedione
1-(3,5-dibromophenyl)-3-(1,2,2,3,4,4-hexafluorocyclobutyl)-1,3-propanedione
1-(3,5-dichlorophenyl)-3-(1,2,2,3,3,4,4,5,5,6,6-undecafluorocyclohexyl)-1,3-propanedione
1-(3,5-dibromophenyl)-3-(1,2,2,3,3,4,4,5,6,6-decafluorocyclohexyl)-1,3-propanedione
1-(3,5-difluorophenyl)-3-(2,2,3,3,4,4,5,5-octafluorocyclopentyl)-1,3-propanedione
1-[3,5-bis(trifluoromethyl)phenyl]-3-(1,1,2,2,2-pentafluoroethyl)-1,3-propanedione
1-[3,5-bis(trifluoromethyl)phenyl]-3-(1,1,2,2-tetrafluoroethyl)-1,3-propanedione
1-[3,5-bis(trifluoromethyl)phenyl]-3-(1,1,2,2,3,3,3-heptafluoropropyl)-1,3-propanedione
1-[3,5-bis(trifluoromethyl)phenyl]-3-(1,1,2,3,3,3-hexafluoropropyl)-1,3-propanedione
1-[3,5-bis(trifluoromethyl)phenyl]-3-(1,1,2,2,3,3,4,4-octafluorobutyl)-1,3-propanedione
1-[3,5-bis(trifluoromethyl)phenyl]-3-(2-trifluoromethyl-1,1,3,3,3-pentafluoropropyl)-1,3-propanedione
1-[3,5-bis(trifluoromethyl)phenyl]-3-(1,2,2,3,3,4-hexafluorocyclobutyl)-1,3-propanedione
1-(5-chloro-3-fluorophenyl)-3-(1,1,2,2,3,3,3heptafluoropropyl)-1,3-propanedione
1-(3-bromo-5-fluorophenyl)-3-(2-trifluoromethyl-1,1,2,3,3,3-hexafluoropropyl)-1,3-propanedione 1-(3-fluoro-5-trifluoromethylphenyl)-3-(1,2,2,3,3,4,4-heptafluorocyclobutyl)-1,3-propanedione 1-(3-chloro-5-trifluoromethylphenyl)-3-(1,2,2,3,3-pentafluorocyclopropyl)-1,3-propanedione 1-(5-bromo-3-chlorophenyl)-3-(1,1,2,2,3,3-hexafluoropropyl)-1,3-propanedione 1-(3-fluoro-5-trifluoromethylphenyl)-3-(1,1,2,2,2-pentafluoroethyl)-1,3-propanedione 1-(5-chloro-3-trifluoromethylphenyl)-3-(1,2,2,3,4,4-hexafluorocyclobutyl)-1,3-propanedione 1-(3-bromo-5-fluorophenyl)-3-(1,1,2,2,3,3,4,4,4-nonafluorobutyl)-1,3-propanedione 1-(3-chloro-5-fluorophenyl)-3-(1,1,2,2-tetrafluoroethyl)-1,3-propanedione 1-(3-bromo-5-chlorophenyl)-3-(2-trifluoromethyl-1,1,3,3,3-pentafluoropropyl)-1,3-propanedione 1-(5-bromo-3-chlorophenyl)-3-(1,2,2,3,3,4,4,5,5,6-decafluorocyclohexyl)-1,3-propanedione The compounds of the present invention are made by processes which are analogous to those in the art for making similar compounds. In general, a 3,5-disubstituted acetophenone is reacted with a small alkyl ester of a perfluoroalkanoic acid, or a derivative thereof such as an acyl halide. The reaction is carried out in the presence of a strong base, such as an alkali metal alkoxide, preferably sodium methoxide or ethoxide, at ambient or moderately elevated or depressed temperatures. As the Examples below indicate, the reaction goes well in short periods of time and economical yields of the product compounds can be obtained.

It is possible to use strong bases, other than the above-described alkali metal alkoxides, in the reaction. For example, alkyllithium compounds, such as n-butyllithium, and alkali metal amides, of which lithium diisopropyl amide is a preferred example, are useful.

When a perfluorocycloalkyl compound is to be made, an alternate synthesis proceeds through the corresponding perfluoroalkyl, preferably trifluoromethyl, compound in the alkali metal salt form. That compound is contacted with a strong base, such as sodium hydride, to form an anion, which is then reacted with the acid fluoride of the desired perfluorocycloalkyl carboxylic acid. The reaction is readily carried out at ambient or moderately elevated temperatures.

The compounds of the present invention are highly acidic in nature and readily form alkali metal salts. Therefore, the products of the above-described processes are routinely obtained in the salt form. If the free acid form is desired, however, it is only necessary to take the product through an acidic step as the reaction mixture is being worked up. For example, a brief wash with a dilute strong acid, such as dilute hydrochloric acid, readily converts a salt to the free acid.

The following preparative Examples are given to assure that the reader can obtain any desired compound of the present invention. The Examples are not intended to limit the scope of the invention in any respect and should not be so construed.

EXAMPLE 1

1-(3,5-difluorophenyl)-3-(1,1,2,2,3,3,3-heptafluoropropyl)-1,3-propanedione, sodium salt Sodium ethoxide was prepared by reacting 0.3 g. of 50% sodium hydride (6.2 mmol. of sodium hydride) and 0.3 g. (6.5 mmol.) of ethanol in 30 ml. of diethyl ether, and to it at room temperature (22°), were added 0.7 g. (2.9 mmol.) of ethyl 2,2,3,3,4,4,4-heptafluorobutyrate. Then 0.4 g. (2.6 mmol.) of 3,5-difluoroacetophenone were added dropwise over a period of ten minutes, and the mixture stirred for one hour. The mixture was poured onto ice along with 50 ml. of a 10% disodium hydrogen phosphate solution. The organic layer was separated, washed with brine, dried over magnesium sulfate, and concentrated under vacuum. The residue was recrystallized from diethyl ether:hexane to provide 0.78 g. of the desired product. Its n.m.r. spectrum on a 250 mHz instrument showed a singlet at δ=6.30 and broad singlets at δ=7.40 and 7.50, respectively.

Analysis calc. for $C_{12}H_4F_9O_2Na$

Theory: C, 38.52; H, 1.08

Found: C, 38.81; H, 1.31

EXAMPLE 2

1-(3,5-dichlorophenyl)-3-(1,1,2,2,3,3,3-heptafluoropropyl)-1,3-propanedione, sodium salt Sodium ethoxide was prepared by reacting 3.6 g. of 50% sodium hydride (75.0 mmol. of sodium hydride) and 3.5 g. (76.0 mmol.) of ethanol in 100 ml. of diethyl ether. The solution was cooled to about 5° and 9.0 g. (37.0 mmol.) of ethyl 2,2,3,3,4,4,4-heptafluorobutyrate were added. Then 7.0 g. (37.0 mmol.) of 3,5-dichloroacetophenone were added and the mixture stirred for two hours. The mixture was poured onto ice along with 50 ml. of a 10% disodium hydrogen phosphate solution. The organic layer was separated, washed with brine, dried over magnesium sulfate, and concentrated under vacuum. The residue was recrystallized from diethyl-ether:hexane to provide approximately 10 g. of the desired product. Its n.m.r. spectrum on a 250 mHz instrument showed singlets at δ =6.35, 7.75, and 7.85, respectively.

Analysis calc. for $C_{12}H_4Cl_2F_7O_2Na$

Theory: C, 35.41; H, 0.99

Found: C, 35.68; H, 1.26

In an analogous manner to that described in Example 2, the following compounds were prepared:

EXAMPLE 3

1-[3,5-Bis(trifluoromethyl)phenyl]-3-(1,1,2,2,3,3,3-heptafluoropropyl)-1,3-propanedione, sodium salt Ethyl 2,2,3,3,4,4,4-heptafluorobutyrate (4.84 g., 20.0 mmol.) and 3,5-bis(trifluoromethyl)-acetophenone (5.0 g., 19.5 mmol.) were reacted to provide 2.5 g. of the title compound. The compound's n.m.r. spectrum on a 250 mHz instrument showed singlets at δ=6.51, 8.23, and 8.35, respectively.

Analysis calc. for $C_{14}H_4F_{13}O_2Na$

Theory: C, 35.46; H, 0.85

Found: C, 35.51; H, 1.08

EXAMPLE 4

1-(3,5-Dichlorophenyl)-3-(1,1,2,2,2-pentafluoroethyl)-1,3-propanedione, sodium salt Ethyl 2,2,3,3,3-pentafluoropropionate (30.0 g., 156.0 mmol.) and 3,5-dichloroacetophenone (23.2 g., 123.0 mmol.) were reacted to provide the title compound. The compound's n.m.r. spectrum on a 250 mHz instrument showed a singlet at δ=6.35 and a broad singlet at δ=7.8 –7.9.

Analysis calc. for $C_{11}H_4Cl_2F_5O_2Na$

Theory: C, 37.00; H, 1.13

Found: C, 36.93; H, 1.40

EXAMPLE 5

1-(3,5-Dichlorophenyl)-3-(1,1,2,2-tetrafluoroethyl)-1,3-propanedione, sodium salt 2,2,3,3-Tetrafluoropropionyl chloride (5.5 g., 33.0 mmol.) and 3,5-dichloroacetophenone (5.6 g., 29.6 mmol.) were reacted to provide the title compound, which was then recrystallized from hexane to provide an off-white solid. The compound's n.m.r. spectrum on a 250 mHz instrument showed a singlet at $\delta=6.30$ (1H); a triplet of triplets at $\delta=6.65$ (1H); a singlet at $\delta=7.80$ (1H); and a singlet at $\delta=7.85$ (2H).

Mass spectrum analysis established that this compound exists as a dimer and a trimer, containing from one to three sodium cations.

Analysis calc. for a trimer of the formula $C_{33}H_{16}Cl_6F_{12}O_6Na_2$

Theory: C, 39.83; H, 1.62
Found: C, 39.81; H, 1.92

EXAMPLE 6

1-(3,5-Dibromophenyl)-3-(1,1,2,2,3,3,3-heptafluoropropyl)-1,3-propanedione, sodium salt Ethyl 2,2,3,3,4,4,4-heptafluorobutyrate (4.0 g., 6.5 mmol.) and 3,5-dibromoacetophenone (4.2 g., 15.0 mmol.) were reacted to provide 5.0 g. of the title compound as a light yellow powder. The product compound had a melting point of 131°–134°. Its n.m.r. spectrum on a 250 mHz instrument showed a singlet at $\delta=6.30$ (1H) and a broad singlet at $\delta=8.00$ (3H).

Mass spectrum analysis established that this compound exists as a dimer, containing one or two sodium cations.

Analysis calc. for a dimer of the formula $C_{24}H_9F_{14}Br_4O_4Na$

Theory: C, 29.75; H, 0.93
Found: C, 29.78; H, 1.05

Representative compounds of the present invention have been tested both in vitro and in vivo to determine the scope of their activity. The following tests are illustrative.

Single Dose—Cattle Systemic Test

Representative compounds were tested in cattle using a single intraruminal injection of the desired dose of the compound dissolved in 10 ml. of polyethylene glycol. The cattle were calves weighing at least 165 kg., housed in environmentally controlled pens. Two calves were used for each compound tested. The calves were fed on a conventional mixed feed which provided adequate nutrients and energy. Feed and water were available to the calves at all times.

Each day, a sample of blood was obtained from the jugular vein of each calf. The blood samples were centrifuged to obtain serum, and the serum was exposed to insects as described below. Thus, the tests evaluated the systemic activity of the compounds, and also the length of time during which the compound persisted in the animal's system.

In one in vitro method used to evaluate compound activity, dental wicks were saturated with the above blood serum and then placed in Petri dishes containing adult stable flies and in test tubes containing blow fly larvae. After 24 hours, the insects were examined and the number of dead counted. A compound was considered to be active, for purposes of the present disclosure, on any day in which at least 50% of the insects were killed upon exposure to the saturated wick.

Certain compounds were further tested by exposing dental wicks saturated with blood serum, per the method described above, to insects for 48 hours rather than 24 hours. After 48 hours, the insects were examined and the number of dead counted. Again, a compound was considered to be active, for purposes of the present disclosure, on any day in which at least 50% of the insects were killed upon exposure to the saturated wick.

The following table reports test results of representative compounds of the present invention. The compounds are identified by their Example numbers above. Insecticidal results are reported in terms of "days of insecticidal activity", indicating the specific test days on which at least 50% of the insects were killed upon exposure to a serum saturated dental wick for either a 24 or 48 hour period.

TABLE I

Insecticidal Activity Following 24 and 48 Hour
In Vitro Exposure of Insects to Cattle Sera

| Compound of Ex. Number | Dose (mg./kg.) | Test Days | 24 Hours L | 24 Hours A | 48 Hours L | 48 Hours A |
|---|---|---|---|---|---|---|
| 3 | 10.0 | 10 | 0 | 2–5, 7–9 | NT | NT |
| 3 | 10.0 | 10 | 0 | 2, 3, 5–8 | NT | NT |
| 2 | 5.0 | 10 | 2–4 | 2–4 | 1–6 | 1–8, 10 |
| 2 | 5.0 | 10 | 2–3 | 2–4 | 1–6 | 1–10 |
| 4 | 5.0 | 10 | 0* | 2–3 | 3–4+ | 3–5+ |
| 4 | 5.0 | 10 | 0* | 0 | 3–4+ | 3–6+ |
| 5 | 5.0 | 10 | 0 | 0 | 0+ | 0+ |
| 5 | 5.0 | 10 | 0 | 0 | 0+ | 0+ |
| 6 | 5.0 | 10 | 0* | 2–3 | NT | NT |
| 6 | 5.0 | 10 | 0* | 3 | NT | NT |

L = Blow Fly Larvae
A = Adult Stable Fly
NT = Not Tested
*Blow Fly Larvae alive but stunted in size (Compound of Example 4 - days 3 and 4, Compound of Example 6 - days 4 and 5).
+Not tested on days 1, 2 or 7–10.

Representative compounds of the present invention were also tested using an in vivo test system comprising placing a chamber containing six starved adult stable flies on the back of the test animal on each test day. The flies were collected daily and the number of dead flies counted. A compound was considered to be active, for purposes of the present discussion, on any day in which at least 50% of the flies had died prior to collection.

The following table presents the in vivo test results. The compounds are identified by their Example numbers above. Insecticidal results are reported in terms of "days of insecticidal activity". Again, the term "days of insecticidal activity" refers to the specific test days in which at least 50% of the adult stable flies had died prior to collection.

TABLE II

In Vivo Insecticidal Activity

| Compound of Example No. | Dose (mg./kg.) | Test Days | Days of Insecticidal Activity |
|---|---|---|---|
| 3 | 10.0 | 10 | 2, 7, 8 |
| 3 | 10.0 | 10 | 6, 7 |

Multiple Dose—Cattle Systemic Test

Representative compounds of the invention were also tested in cattle using multiple intraruminal injections of the desired dose of the compound. The multiple injections consisted of daily administration of a single intra-ruminal injection for a period ranging from 10 to 18 days. The cattle tested were similar in size to those described for the single dose test detailed above. Two calves were used for each compound and dose tested. The calves were also fed and watered as previously described.

The daily dose of compound to be tested was prepared using one of two methods. In one method the desired dose was prepared, daily, prior to administration, by dissolving the required daily amount of test compound in 5 ml. of polyethylene glycol. In an alternative method the entire amount of compound required for the test was dissolved in a sufficient amount of polyethylene glycol such that the resulting solution contained approximately 5 ml. of polyethylene glycol for each day of testing. The total volume of material thus prepared was then placed in a capped serum bottle which was suitable for metering out the desired daily dose.

Approximately 24 hours after the previous day's intraruminal dose had been administered, and just before the current day's dose was to be administered, a sample of blood was obtained from the jugular vein of each calf tested. The blood samples were centrifuged to obtain serum and the serum exposed to adult stable flies and blow fly larvae per the 24 and 48 hour in vitro test system described previously. In addition, certain compounds were also tested using the in vivo adult stable fly test described above.

The calves were given daily intraruminal injections for periods ranging from 10 to 18 days and then the injections were stopped. Both in vitro and in vivo testing was continued for several days beyond the administration period, preferably until no further insecticidal activity was observed. Thus, the tests evaluated the systemic activity of the compounds, and also the length of time during which the compound persisted in the animal's system.

Tables III and IV report test results of representative compounds. The compounds are identified by their Example numbers above. Table III reports insecticidal activity in the 24 and 48 hour in vitro test system. Table IV reports insecticidal activity against adult stable flies in the in vivo test system. Insecticidal results, in both tables, are reported in terms of "days of insecticidal activity". The term "days of insecticidal activity" is used in the same manner as in Tables I and II above.

TABLE III

Insecticidal Activity Following 24 and 48 Hour In Vitro Exposure of Insects to Cattle Sera

| Compound of Example No. | Daily Dose (mg/kg/day) | Dose Time (Days) | Test Days | 24 Hours L | 24 Hours A | 48 Hours L | 48 Hours A |
|---|---|---|---|---|---|---|---|
| 2 | 1.00 | 18 | 26 | 6–26 | 3–26 | NT | NT |
| 2 | 1.00 | 18 | 21* | 5–21 | 3–21 | NT | NT |
| 2 | 0.50 | 17 | 25 | 0 | 10–11 | 7–16, 18–19 | 4, 6–21 |
| 2 | 0.50 | 17 | 25 | 0 | 12 | 8–15 | 4, 6–19 |
| 2 | 0.35 | 17 | 25 | 0 | 0 | 0 | 7, 9–18 |
| 2 | 0.35 | 17 | 25 | 0 | 0 | 0 | 6, 8–18 |
| 2 | 0.20 | 17 | 25 | 0 | 0 | 0 | 0 |
| 2 | 0.20 | 17 | 25 | 0 | 0 | 0 | 0 |
| 4 | 1.50 | 10 | 19 | 4–18 | 2, 4–19 | 2–19 | 2–19 |
| 4 | 1.50 | 10 | 19 | 4–16 | 3–19 | 2–18 | 2–19 |
| 4 | 1.00 | 18 | 26 | 5–23 | 3–25 | NT | NT |
| 4 | 1.00 | 18 | 26 | 5–22 | 3–25 | NT | NT |
| 4 | 0.75 | 10 | 19 | 6–11 | 5, 8–14 | 4–13 | 3–17 |
| 4 | 0.75 | 10 | 19 | 7–10 | 9–11 | 4–13 | 4–17 |
| 4 | 0.50 | 10 | 19 | 0 | 10–11 | 6–12 | 4, 6–18 |
| 4 | 0.50 | 10 | 19 | 0 | 10–12 | 6–12 | 4, 6–16, 18 |
| 4 | 0.30 | 17 | 25 | 0 | 0 | 0 | 4, 9, 12 |
| 4 | 0.30 | 17 | 25 | 0 | 0 | 0 | 4, 8, 10–11, 16 |
| 5 | 1.00 | 18 | 26 | 0 | 4, 6–9, 11, 17 | 0 | 3–18 |
| 5 | 1.00 | 18 | 26 | 0 | 6, 8, 9, 11, 17 | 0 | 5–18 |

L = Blow Fly Larvae
A = Adult Stable Fly
NT = Not Tested
*Test animal died on day 21

TABLE IV

In Vivo Insecticidal Activity

| Compound of Ex. Number | Dose (mg./kg./day) | Dose Time (Days) | Test Days | Days of Insecticidal Activity |
|---|---|---|---|---|
| 2 | 1.00 | 18 | 26⁺ | 4–13, 15–22, 25–26 |
| 2 | 1.00 | 18 | 21* | 1, 6–12, 15–21 |
| 4 | 1.00 | 18 | 26° | 4–8, 10–13, 15–26 |
| 4 | 1.00 | 18 | 26⁺ | 5–13, 15–26 |

⁺Data not available for day 14.
*Test animal died on day 21; Data not available for days 2–5 and 13–14.
°Data not available for days 9 and 14.

Tick Test

The activity of the compounds of the invention against Lone Star ticks, *Amblyomma americanum*, was determined as follows. Two calves were given a daily 1 mg./kg. intraruminal injection of a solution consisting of the required amount of the compound of Example 2 dissolved in 5 ml. of polyethylene glycol. Two other calves were given a daily 1 mg./kg. intraruminal injection of a solution consisting of the required amount of the compound of Example 4 dissolved in 5 ml. of polyethylene glycol. Finally, two other calves were used as control calves, with one calf given 5 ml. of polyethylene glycol each day while the other calf was left untreated. All treatments continued for a total of 18 days.

Forty (20 female and 20 male) adult Lone Star ticks were placed on each calf seven days after the treatments described above were started. In addition, 30 Lone Star tick nymphs were placed on each test animal at this same point in time. Eleven days later the calves were examined to assess the compounds' efficacy on adult and nymph tick viability. The results of this test are presented in Table V below.

TABLE V

Compound Efficacy Against Adult and Nymph Ticks

| Calf Treatment | Tick Viability After 11 Days Exposure |
|---|---|
| 1 mg./kg./day of Compound of Example 2 in 5 ml. of polyethylene glycol | All nymphs dead; No adult ticks repleted; All female adult ticks dead. |
| 1 mg./kg./day of Compound of Example 4 in 5 ml. of polyethylene glycol | All nymphs dead; No adult ticks repleted; All female adult ticks dead. |
| 5 ml./day of polyethylene glycol | 16/30 nymphs alive; All adult ticks repleted; All female adult ticks alive and normal in egg production. |
| No treatment | 18/30 nymphs alive; All adult ticks repleted; All female adult ticks alive and normal in egg production. |

The activity of the compound of Example 3 against Lone Star ticks was determined as follows. Two calves received a 10 mg./kg. single intraruminal dose of the required amount of the compound of Example 3 dissolved in 10 ml. of polyethylene glycol. One calf, used as a control, was given 10 ml. of polyethylene glycol. Forty (20 female and 20 male) adult Lone Star ticks were placed on each calf three days prior to treatment in order to provide time for the ticks to attach. In addition, thirty Lone Star nymphs were placed on each calf one day prior to treatment. The ticks were allowed to feed to repletion and the engorged ticks were collected daily and held at 26° and 96% relative humidity to assess the test compound's efficacy on tick viability. The results of this test indicated that the compound of Example 3 had no activity against ticks under these test conditions.

Methods of Use

The method of the present invention is carried out by administering a compound of the invention to a host animal to control insect and acarina parasites. Administration to the animal may be by the oral or percutaneous routes.

Parasitic insects and acarina include species that are bloodsucking as well as flesh eating and are parasitic during all of their life cycle or only part of their life cycle, such as only the larval or only the adult stage. Representative species include the following:

| horse fly | Tabanus spp. |
| stable fly | Stomoxys calcitrans |
| black fly | Simulium spp. |
| horse sucking louse | Haematopinus asini |

-continued

| mange mite | Sarcoptes scabiei |
| scab mite | Psoroptes equi |
| horn fly | Haematobia irritans |
| cattle biting louse | Bovicola bovis |
| shortnosed cattle louse | Haematopinus eurysternus |
| longnosed cattle louse | Linognathus vituli |
| tsetse fly | Glossina spp. |
| cattle follicle mite | Demodex bovis |
| cattle tick | Boophilus microplus and B. decoloratus |
| Gulf Coast tick | Amblyomma maculatum |
| Lone Star tick | Amblyomma americanum |
| ear tick | Otobius megnini |
| Rocky Mountain wood tick | Dermacentor andersoni |
| screwworm fly | Cochliomyia hominivorax |
| assassin bug | Reduvius spp. |
| mosquito | Culiseta inornata |
| brown ear tick | Rhipicephalus appendiculatus |
| African red tick | Rhipicephalus evertsi |
| bont tick | Amblyomma sp. |
| bont legged tick | Hyalomma sp. |
| hog louse | Haematopinus suis |
| chigoe | Tunga penetrans |
| body louse | Haematopinus ovillus |
| foot louse | Linognathus pedalis |
| sheep ked | Melophagus ovinus |
| sheep scab mite | Psoroptes ovis |
| greenbottle fly | Phaenicia sericata |
| black blow fly | Phormia regina |
| secondary screw-worm | Cochliomyia macellaria |
| sheep blow fly | Phaenicia cuprina |
| bed bug | Cimex lectularius |
| Southern chicken flea | Echidnophaga gallinacea |
| fowl tick | Argas persicus |
| chicken mite | Dermanyssus gallinae |
| scalyleg mite | Knemidokoptes mutans |
| depluming mite | Knemidokoptes gallinae |
| dog follicle mite | Demodex canis |
| dog flea | Ctenocephalis canis |
| American dog tick | Dermacentor variabilis |
| brown dog tick | Rhipicephalus sanguineus |

The method of the invention may be used to protect economic and companion animals from ectoparasites. For example, the compounds may beneficially be administered to horses, cattle, sheep, pigs, goats, dogs, cats and the like, as well as to exotic animals such as camels, llamas, deer and other species which are commonly referred to as wild animals. The compounds may also beneficially be administered to poultry and other birds, such as turkeys, chickens, ducks and the like. Preferably, the method is applied to economic animals, and most preferably to cattle and sheep.

The claimed compounds display systemic ectoparasiticidal activity. The compounds have the ability to permeate the tissues of a host animal to which one of the compounds has been administered. Insect parasites which then consume blood or other living tissues of the host animal are thereby killed. Hence, the term "controlling", as defined for purposes of the present disclosure, entails the destruction of an insect population by killing the undesired insects after thay have consumed blood or other living tissue from the host animal. The compounds can be administered by oral or percutaneous routes, and are preferably formulated prior to administration.

Percutaneous administration is conveniently accomplished by intraperitoneal, intraruminal and intravenous injection of an injectable formulation.

Oral administration is a particularly preferred route of administration. The rate, timing, and manner of effective administration will vary widely with the identity of the parasite, the degree of parasiticidal attack, and other factors. Administration can be made periodically over the entire lifespan of the host, or for only a peak season of parasitic attack. In general, effective parasite control is achieved at administration rates of from about 5 to about 100 mg./kg. Oral administration may be performed by mixing the compound in the animals' feed or drinking water, or by administering dosage forms such as tablets, capsules, boluses, or implants.

Since ectoparasitic attack generally takes place during a substantial portion of the host animal's lifespan, it is preferred to orally administer the compounds of the present invention in a dosage form capable of providing sustained release over a period of time. Conventional procedures include the use of a matrix which physically inhibits dissolution, where the matrix is a waxy semisolid, such as a vegetable wax, a high molecular weight polyethylene glycol, or a copolymeric matrix such as that described in Nevin, U.S. Pat. No. 4,273,920. A good way to administer the compounds is by means of a sustained-action bolus, such as those of Laby, U.S. Pat. No. 4,251,506, Davis et al., U.S. Pat. No. 4,649,042 and Simpson, British Patent 2,059,767. Sustained release of the compounds of the present invention can also be achieved by the use of an implant such as from a silicone-containing rubber.

Usually, the compounds are formulated into ectoparasiticidal compositions which comprise a compound of the present invention and a physiologically-acceptable carrier. Such formulations are well known to those skilled in the art, for example by dissolving or dispersing the compound in one of many physiologically-acceptable adjuvants or diluents.

The compounds can be formulated for oral administration in the usual forms, such as drenches, tablets, or capsules. Such compositions, of course, require orally-acceptable inert carriers. The compounds can also be formulated as an injectable solution or suspension, for intraperitoneal, intraruminal or intravenous injection.

In some applications, the compounds are conveniently formulated as one component of a standard animal feed. In this embodiment, it is usual to formulate the compound first as a premix in which the compound is dispersed in a liquid or particulate solid carrier. The premix can contain from about 2 to 250 grams of compound per pound. The premix is then, in turn, formulated into the ultimate feed by conventional mixing.

The following exemplary compositions illustrate the sort of formulations used to practice the present invention.

| Feed Premix | |
|---|---|
| Compound of Example 2 | 10% |
| Rice hulls | 85 |
| Light mineral oil | 5 |
| Feed Premix | |
| Compound of Example 4 | 25% |
| Alfalfa meal | 60 |
| Powdered clay | 5 |
| Molasses | 10 |
| Suspension | |
| Compound of Example 1 | 30% |
| Naphthalenesulfonate salt | 5 |
| Nonionic surfactant | 5 |
| Fumed silica | 1 |
| Water | 59 |
| Drip-On Solution | |
| Compound of Example 5 | 20% |
| Nonionic surfactant | 0.8 |
| Propylene glycol | 15 |
| Water | 64.2 |
| Drip-On Suspension | |
| Compound of Example 6 | 10 |
| Nonionic surfactant | 1 |
| Light mineral oil | 89 |
| Injectable Solution | |
| Compound of Example 4 | 15% |
| Propylene glycol | 85 |
| Injectable Solution | |
| Compound of Example 2 | 5% |
| Polyethylene glycol | 95 |
| Injectable Suspension | |
| Compound of Example 4 | 25% |
| Propylene glycol | 15 |
| Water | 60 |
| Injectable Suspension | |
| Compound of Example 5 | 30% |
| Polyvinylpyrrolidone | 2 |
| Water | 68 |

We claim:

1. A pharmaceutically acceptable ectoparasiticidal composition suitable for oral or percutaneous administration to an economic or companion animal such as to kill insect and acarina parasites consuming the blood or other living tissue of the animal comprising a compound of the formula

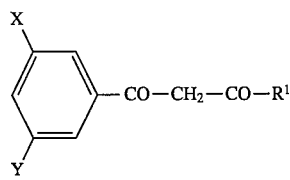

wherein
$R^1$ is a $C_2$–$C_4$ perfluoroalkyl group or a $C_3$–$C_6$ perfluorocycloalkyl group, and X and Y are the same and are selected from the group consisting of chloro, bromo, fluoro or trifluoromethyl; or a sodium potassium or lithium salt thereof,
together with a physiologically acceptable inert carrier.

2. An ectoparasiticidal composition of claim 1 in the form of a feed premix wherein the inert carrier is an orally acceptable inert carrier.

3. An ectoparasiticidal composition of claim 1 in the form of an orally administered sustained release device wherein the inert carrier comprises a matrix which physically inhibits dissolution.

4. An ectoparasiticidal composition of claim 1 in the form of an orally administered sustained release device wherein the inert carrier comprises a matrix of a polyethyleneglycol of molecular weight sufficiently high to physically inhibit dissolution.

5. An ectoparasiticidal composition of claim 3 wherein the matrix which physically inhibits dissolution is a copolymeric matrix comprised of glycolic acid and lactic acid.

6. An ectoparasiticidal composition of claim 1 wherein $R^1$ is a $C_2$–$C_4$ perfluoroalkyl group.

7. An ectoparasiticidal composition of claim 6 wherein $R^1$ is a $C_2$–$C_3$ perfluoroalkyl group.

8. An ectoparasiticidal composition of claim 7 wherein X and Y are the same and are chloro, bromo or fluoro.

9. An ectoparasiticidal composition of claim 8 wherein X and Y are both chloro.

10. An ectoparasiticidal composition of claim 1 wherein said compound is 1-(3,5-dichlorophenyl)-3-(1,1,2,2,3,3,3-heptafluoropropyl)-1,3-propanedione or a sodium, potassium or lithium salt thereof.

11. An ectoparasiticidal composition of claim 1 wherein said compound is the sodium salt of 1-(3,5-dichlorophenyl)-3-(1,1,2,2,3,3,3-heptafluoropropyl)-1,3-propanedione.

12. An ectoparasiticidal composition of claim 1 wherein said compound is 1-(3,5-dichlorophenyl)-3-(1,1,2,2-tetrafluoroethyl)-1,3-propanedione or a sodium, potassium or lithium salt thereof.

13. An ectoparasiticidal composition of claim 1 wherein said compound is the sodiron salt of 1-(3,5-dichlorophenyl)-3-(1,1,2,2-tetrafluoroethyl)-1,3-propanedione.

14. An ectoparasiticidal composition of claim 1 wherein said compound is 1-(3,5-dichlorophenyl)-3-(1,1,2,2,2-pentafluoroethyl)-1,3-propanedione, or sodium or lithium salt thereof.

15. An ectoparasiticidal composition of claim 1 wherein said compound is the sodium salt of 1-(3,5-dichlorophenyl)-3-(1,1,2,2,2-pentafluoroethyl)-1,3-propanedione.

16. An ectoparasiticidal composition of claim 3, wherein the composition is in the form of a tablet, capsule or bolus.

17. An ectoparasiticidal composition of claim 1, wherein the composition is in the form of an animal feed.

18. An ectoparasiticidal composition of claim 2, wherein the composition comprises rice hulls and light mineral oil or comprises Alfalfa meal, powdered clay and molasses.

19. An ectoparasiticidal composition of claim 18, wherein the compound of the formula shown, the rice hulls and light mineral oil are provided in ratio approximately 10%:85%:5%.

20. An ectoparasiticidal composition of claim 18, wherein the compound of the formula shown, the Alfalfa meal, powdered clay and molasses are provided in ratio approximately 25%:60%:5%:10%.

21. An ectoparasiticidal composition of claim 17, wherein the compound shown is provided as a drench suspension including naphthalene sulfonate salt, a non-ionic surfactant, fumed silica and water.

22. An ectoparasiticidal composition of claim 21, wherein the compound of the formula shown, the naphthalene sulfonate salt, non-ionic surfactant, fumed silica and water are provided in ratio approximately 30%: 5%:5%:1%:59%.

23. An ectoparasiticidal composition of claim 17, wherein the compound is added to a standard animal feed in the form of a drip-on solution including non-ionic surfactant propylene glycol and water.

24. An ectoparasiticidal composition of claim 23, wherein the compound, non-ionic surfactant, propylene glycol and water are provided in ratio 20%:0.8%:15%:64.2%.

25. An ectoparasiticidal composition of claim 17, wherein the compound is added to a standard animal feed in the form of a drip-on suspension including non-ionic surfactant and light mineral off.

26. An ectoparasiticidal composition of claim 25, wherein the compound, non-ionic surfactant and light mineral off are provided in ratio 10%:1%:89%.

27. An ectoparasiticidal composition of claim 1 being an injectable solution of the compound in polyethylene glycol or polypropylene glycol.

28. An ectoparasiticidal composition of claim 1 being an injectable suspension of one of glycol or polyvinyl pyrrolidone together with water.

29. An ectoparasiticidal composition of claim 1 in the form of an injectable dose of 5 or 10 ml of polyethylene glycol or polypropylene glycol.

30. An ectoparasiticidal composition of claim 1 in the form of an implant.

31. An ectoparasiticidal composition of claim 11 in the form of a silicone containing rubber implant.

\* \* \* \* \*